United States Patent
Kim et al.

(12) 
(10) Patent No.: US 9,062,179 B2
(45) Date of Patent: Jun. 23, 2015

(54) ESTER COMPOSITION, METHOD OF PREPARING THE SAME AND RESIN COMPOSITION INCLUDING THE SAME

(71) Applicant: LG CHEM. LTD., Seoul (KR)

(72) Inventors: Hyun Kyu Kim, Daejeon (KR); Mi Yeon Lee, Daejeon (KR); Dong Hyun Ko, Daejeon (KR); Chil Eui Hong, Daejeon (KR); Gyu Il Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/150,472

(22) Filed: Jan. 8, 2014

(65) Prior Publication Data

US 2014/0336319 A1 Nov. 13, 2014

Related U.S. Application Data

(63) Continuation of application No. PCT/KR2013/006329, filed on Jul. 15, 2013.

(30) Foreign Application Priority Data

| May 8, 2013 | (KR) | 10-2013-0051617 |
| Jun. 14, 2013 | (KR) | 10-2013-0068197 |
| Jul. 15, 2013 | (KR) | 10-2013-0082973 |

(51) Int. Cl.
*C08K 5/12* (2006.01)
*C07C 67/40* (2006.01)

(52) U.S. Cl.
CPC .. *C08K 5/12* (2013.01); *C07C 67/40* (2013.01)

(58) Field of Classification Search
CPC .......... C07C 67/82; C07C 67/40; C07C 67/42

USPC ...... 560/64; 524/314, 321; 106/311
See application file for complete search history.

(56) References Cited

U.S. PATENT DOCUMENTS

| 7,361,779 B1 * | 4/2008 | Holt et al. ............... 560/76 |
| 7,732,634 B2 * | 6/2010 | Soled et al. ............. 562/509 |
| 2007/0037926 A1 | 2/2007 | Olsen et al. |
| 2007/0179229 A1 | 8/2007 | Grass |
| 2008/0054089 A1 * | 3/2008 | Oldfield et al. ............ 239/60 |
| 2008/0057317 A1 | 3/2008 | Kettner et al. |

FOREIGN PATENT DOCUMENTS

| JP | 2002-332394 | 11/2002 |
| KR | 10-2007-0075341 | 7/2007 |
| KR | 10-2013-0035493 A | 4/2013 |
| WO | 2010071717 A1 | 6/2010 |

* cited by examiner

*Primary Examiner* — Tae H Yoon

(74) *Attorney, Agent, or Firm* — McKenna Long & Aldridge, LLP

(57) ABSTRACT

An ester composition including terephthalate compounds substituted with a non-hybrid and non-branch type alkyl group, a hybrid and branch type alkyl group, and a non-hybrid and branch type alkyl group, respectively by 0.5 wt % to 9.5 wt %, by 14.5 wt % to 43.8 wt %, and 46.7 wt % to 85 wt % based on the total weight of the ester composition, a method of preparing the same, and a resin composition including the same are provided. The ester composition has a short absorption time with respect to the resin and short fusion time and improves the processability of the resin composition. In addition, good physical properties may be provided when manufacturing a sheet and a compound such as a cable, an interior of a car, a film, a sheet, a tube, a wallpaper, a toy, a flooring material, and the like.

9 Claims, No Drawings

ESTER COMPOSITION, METHOD OF PREPARING THE SAME AND RESIN COMPOSITION INCLUDING THE SAME

This application is a Continuation Bypass of International Application PCT/KR2013/006329, with an international filing date of Jul. 15, 2013, which claims priority to and the benefit of Korean Patent Application No. 10-2013-0051617, filed May 8, 2013, Korean Patent Application No. 10-2013-0068197, filed Jun. 14, 2013, and Korean Patent Application No. 10-2013-0082973, filed Jul. 15, 2013, all of which are incorporated herein by reference in their entirety.

TECHNICAL FIELD

The present invention relates to an ester composition, a method of preparing the same, and a resin composition including the same, and more particularly, to an ester composition including terephthalate compounds substituted with a non-hybrid and non-branch type alkyl group, a hybrid and branch type alkyl group, and a non-hybrid and branch type alkyl group by specific amount ranges, a method of preparing the same, and a resin composition including the same.

BACKGROUND OF THE INVENTION

In general, a plasticizer includes an ester compound formed through the reaction of an alcohol with a polycarboxylic acid such as phthalic acid and adipic acid. Commercially significant examples of the plasticizer includes an adipate of C8, C9 and C10 alcohols, for example, di(2-ethylhexyl)adipate, diisononyl adipate, diisodecyl adipate, and the like; and a phthalate of C8, C9 and C10 alcohols, for example, di(2-ethylhexyl)phthalate, diisononyl phthalate, diisodecyl phthalate, and the like.

Particularly, the di(2-ethylhexyl)phthalate may be used after forming a plastisol and conducting dry mixing, for manufacturing a toy, a film, shoes, a paint composition, a flooring material, gloves, a wallpaper, a synthetic leather, a sealant, a tarpaulin, a coating agent on the floor of a car, a furniture, foam mats and a soundproof panel. In addition, the di(2-ethylhexyl)phthalate may be used for manufacturing a package and an insulation of a PVC cable, and a calendered plastic PVC product.

As an ester composition used as the plasticizer, di(2-ethylhexyl)phthalate is widely used nowadays. However, the compound is an environmental hormone disturbing an endocrine organ and is harmful to human body. In addition, the improvement of the processability of a resin, the absorption time of the resin, the degree of migration loss, and a thermal stability is limited when using the compound.

Thus, an environment-friendly ester composition which may sufficiently improve all physical properties including the processability of the resin, the absorption time of the resin, the degree of the migration loss, and the thermal stability, and a method of preparing the same are necessary.

SUMMARY OF THE INVENTION

An aspect of the present invention provides an ester composition having a short absorption time with respect to a resin and a short fusion time to improve the processability of the resin, and providing good physical properties when manufacturing a sheet and a compound such as a cable, an interior of a car, a film, a sheet, a tube, a wallpaper, a toy, a flooring material, and the like.

Another aspect of the present invention provides a method of preparing the ester composition.

Another aspect of the present invention provides a resin composition including the ester composition.

According to an aspect of the present invention, there is provided an ester composition including terephthalate compounds substituted with a non-hybrid and non-branch type alkyl group, a hybrid and branch type alkyl group, and a non-hybrid and branch type alkyl group, respectively by 0.5 wt % to 9.5 wt %, by 14.5 wt % to 43.8 wt %, and 46.7 wt % to 85 wt % based on the total weight of the ester composition.

According to another aspect of the present invention, there is provided a method of preparing the ester composition including conducting a transesterification reaction of di(2-ethylhexyl)terephthalate (DEHTP) with butyl alcohol.

According to another aspect of the present invention, there is provided a resin composition including the ester composition and a resin.

ADVANTAGEOUS EFFECTS

The ester composition in accordance with an example embodiment of the inventive concept has a short absorption time with respect to a resin and a short fusion time to improve the processability of the resin, and providing good physical properties when manufacturing a sheet and a compound such as a cable, an interior of a car, a film, a sheet, a tube, a wallpaper, a toy, a flooring material, and the like.

DETAILED DESCRIPTION OF THE PREFERRED EMBODIMENT

Exemplary embodiments of the present invention will now be described in detail to assist the understanding of the inventive concept.

Unless otherwise defined, all terms and words used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In accordance with an example embodiment of the inventive concept, an ester composition including terephthalate compounds substituted with a non-hybrid and non-branch type alkyl group, a hybrid and branch type alkyl group, and a non-hybrid and branch type alkyl group, respectively by 0.5 wt % to 9.5 wt %, by 14.5 wt % to 43.8 wt %, and 46.7 wt % to 85 wt % based on the total weight of the ester composition, is provided.

In accordance with an example embodiment of the present invention, the ester composition has a short absorption time with respect to a resin and a short fusion time to improve the processability of the resin, and provides good physical properties when manufacturing a sheet and a compound such as a cable, an interior of a car, a film, a sheet, a tube, a wallpaper, a toy, a flooring material, and the like, by including specific amount ranges of terephthalate compounds substituted with a non-hybrid and non-branch type alkyl group, a hybrid and branch type alkyl group, and a non-hybrid and branch type alkyl group, particularly, by including the terephthalate compound substituted with the non-hybrid and non-branch type alkyl group by 0.5 wt % to 9.5 wt % based on the total weight of the ester composition.

In accordance with an example embodiment of the inventive concept, the terephthalate compounds substituted with the non-hybrid and non-branch type alkyl group, the hybrid and branch type alkyl group, and the non-hybrid and branch type alkyl group, may be included by 1 wt % to 8.5 wt %, by 15.8 wt % to 42 wt %, and by 49.5 wt % to 83.2 wt % based on the total weight of the ester composition.

Particularly, the weight ratio of the terephthalate compound substituted with the hybrid and branch type alkyl group with respect to the terephthalate compound substituted with the non-hybrid and non-branch type alkyl group is from 4.6 to 29, and is preferably 5 to 17.

In accordance with an example embodiment of the inventive concept, physical properties such as hardness, tensile strength, elongation rate, migration loss, sheet weight loss after heating, heat stability, and accelerated weathering (QUV), besides the processability with the resin such as the absorption time and the fusion time may be further improved within the weight ratio range.

The terms "non-hybrid and non-branch type" used in the present application mean, unless specifically mentioned, a structure including two kinds of linear hydrocarbons including the same substituted alkyl groups without a branched chain at symmetric sites of a phenyl group.

In addition, the terms "hybrid and branch type" used in the present application mean, unless specifically mentioned, a structure including different substituted alkyl groups at symmetric sites of a phenyl group with one kind of branched chain. For example, in the terephthalate compound substituted with the hybrid and branch type alkyl group, when one of two alkyl groups substituted at the symmetric sites of the phenyl group is a branch type alkyl group, the other alkyl group is a non-branch type alkyl group.

In the hybrid and branch type alkyl substituted terephthalate compound, the branch type alkyl group may be the same as the branch type alkyl group in the non-hybrid and branch type alkyl substituted terephthalate compound. The non-branch type alkyl group in the hybrid and branch type alkyl substituted terephthalate compound may be the same as the non-branch type alkyl group in the non-hybrid and non-branch type alkyl substituted terephthalate compound.

Further, the terms "non-hybrid and branch type" used in the present application means, unless specifically mentioned, a structure including the same substituted alkyl groups at the symmetric site of a phenyl group and having two kinds of branched chains.

The substituted alkyl group may be a hydrocarbon having 3 to 10 carbon atoms, and particularly, may be one independently selected from hydrocarbons having 3 to 4 carbon atoms, and hydrocarbons having 6 to 10 carbon atoms when considering the easy processability (plasticizing efficiency) and migration loss according to rapid absorption time with a resin.

In accordance with an example embodiment of the inventive concept, the non-hybrid and non-branch type alkyl substituted terephthalate compound may be dibutyl terephthalate (DBTP) of the following Chemical Formula 1.

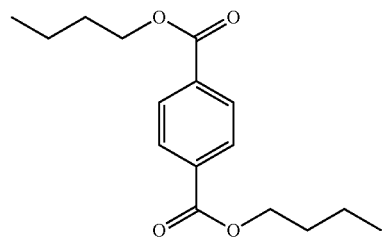

[Chemical Formula 1]

In addition, in accordance with an example embodiment of the inventive concept, the hybrid and branch type alkyl substituted terephthalate compound may be 1-butyl 4-(2-ethylhexyl)terephthalate (BEHTP) of the following Chemical Formula 2.

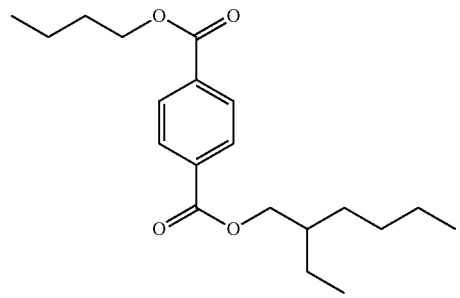

[Chemical Formula 2]

In addition, in accordance with an example embodiment of the inventive concept, the non-hybrid and branch type alkyl substituted terephthalate compound may be di-(2-ethylhexyl) terephthalate (DEHTP) of the following Chemical Formula 3.

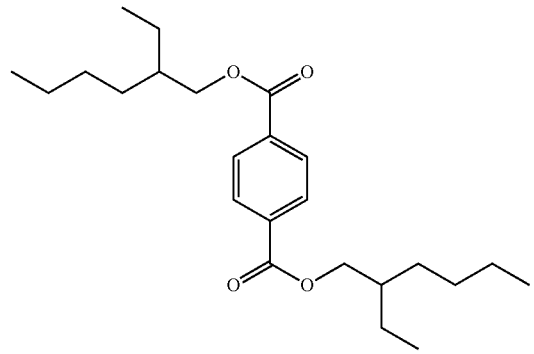

[Chemical Formula 3]

The ester composition may be an ether-free composition and exhibits good plasticizing efficiency and good workability.

The ether-free means that the ether component included in the ester composition is 1,000 ppm or less, 100 ppm or less, or 10 ppm or less.

In accordance with an example embodiment of the inventive concept, transesterification reaction of the di-(2-ethylhexyl)terephthalate (DEHTP) of the following Chemical Formula 3 with butyl alcohol of the following Chemical Formula 4 is conducted, and a method of preparing an ester composition including the compounds of the Chemical Formulae 1 to 3 is provided.

[Chemical Formula 3]

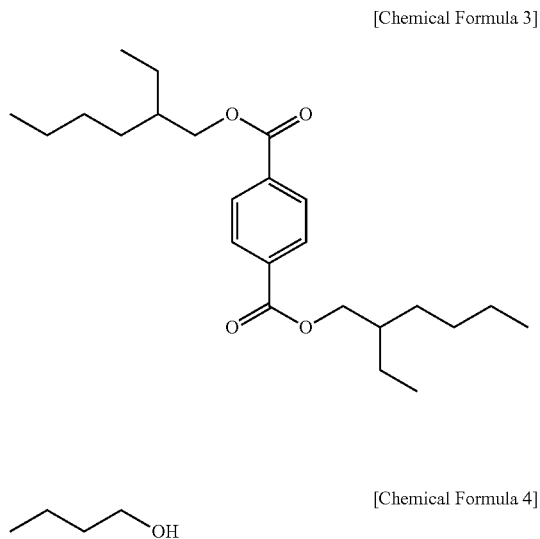

[Chemical Formula 4]

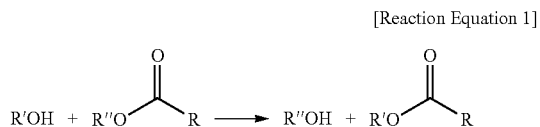

The "transesterification reaction" used in the present application means a reaction between an alcohol and an ester to interchange R" in the ester with R' in the alcohol as illustrated in the following Reaction Equation 1.

[Reaction Equation 1]

$$R'OH + R''O\overset{O}{\underset{}{\diagup\!\!\!\diagdown}}R \longrightarrow R''OH + R'O\overset{O}{\underset{}{\diagup\!\!\!\diagdown}}R$$

In accordance with an example embodiment of the inventive concept, through the transesterification reaction, the dibutyl terephthalate (DBTP) of the above Chemical Formula 1 may be formed when the butoxide ($C_4H_9O$—) of the butyl alcohol of the above Chemical Formula 4 attacks the carbon atoms in two ester groups (RCOOR") substituted at the phenyl group in the di-(2-ethylhexyl)terephthalate (DEHTP) of the above Chemical Formula 3; and the 1-butyl 4-(2-ethylhexyl)terephthalate (BEHTP) may be formed when the butoxide ($C_4H_9O$—) of the butyl alcohol of the above Chemical Formula 4 attacks the carbon atom in one ester group (RCOOR") substituted at the phenyl group in the di-(2-ethylhexyl)terephthalate (DEHTP) of the above Chemical Formula 3. The di-(2-ethylhexyl)terephthalate (DEHTP) of the above Chemical Formula 3 may remain as unreacted portion.

Thus, in accordance with an example embodiment of the inventive concept, the ester composition prepared through the transesterification reaction may include all of the three compounds, the dibutyl terephthalate (DBTP) of the above Chemical Formula 1, the 1-butyl 4-(2-ethylhexyl)terephthalate (BEHTP) of the above Chemical Formula 2, and the di-(2-ethylhexyl)terephthalate (DEHTP) of the above Chemical Formula 3. The component ratio of the ester composition may be controlled by the amount added of the butyl alcohol of the above Chemical Formula 4.

In accordance with an example embodiment of the inventive concept, the ester composition may include, in order of amount included, the di-(2-ethylhexyl)terephthalate (DEHTP) of the above Chemical Formula 3, the 1-butyl 4-(2-ethylhexyl)terephthalate (BEHTP) of the above Chemical Formula 2, and the dibutyl terephthalate (DBTP) of the above Chemical Formula 1. However, when the amount of the butyl alcohol increases, the mole fraction of the di-(2-ethylhexyl) terephthalate (DEHTP) participating in the transesterification reaction may be increased. In this case, the amount of the dibutyl terephthalate (DBTP) of the above Chemical Formula 1 and the 1-butyl 4-(2-ethylhexyl)terephthalate (BEHTP) of the above Chemical Formula 2 may be increased in the ester composition.

Correspondingly, the amount of unreacted di-(2-ethylhexyl)terephthalate (DEHTP) of the above Chemical Formula 3 may be decreased.

In accordance with an example embodiment of the inventive concept, the amount of the butyl alcohol is from 4 parts by weight to 23 parts by weight, preferably from 5 parts by weight to 20 parts by weight based on 100 parts by weight of the di-(2-ethylhexyl)terephthalate (DEHTP), so as to include the dibutyl terephthalate (DBTP) of the above Chemical Formula 1 in the ester composition of 0.5 wt % to 9.5 wt %, and preferably, 1 wt % to 8.5 wt % based on the total weight of the ester composition.

The mole ratio of the di-(2-ethylhexyl)terephthalate (DEHTP) and the butyl alcohol is, for example, 1:0.005 to 5.0, 1:0.2 to 2.5, or 1:0.3 to 1.5. An ester plasticizer having high process efficiency and excellent improving effect of processability may be obtained within the above-described range.

In accordance with an example embodiment of the inventive concept, the transesterification reaction is conducted at a temperature from 120° C. to 190° C., preferably, 135° C. to 180° C., and more preferably, 141° C. to 179° C. for from 10 minutes to 10 hours, preferably, 30 minutes to 8 hours, and more preferably, 1 hour to 6 hours. In the above-described temperature range and reaction time range, an ester composition having a desired component ratio may be effectively obtained. The reaction time may be calculated from the reaching point of a reaction temperature after increasing the temperature of reactants.

In accordance with an example embodiment of the inventive concept, the transesterification reaction may be conducted under an acid catalyst or a metal catalyst. In this case, the reaction time may be decreased.

The acid catalyst may be sulfuric acid, methanesulfonic acid or p-toluenesulfonic acid, and the metal catalyst may be an organic metal catalyst, a metal oxide catalyst, a metal salt catalyst or a metal itself.

The metal may be one selected from the group consisting of tin, titanium and zirconium, or a mixture of two or more thereof.

In accordance with an example embodiment of the inventive concept, a step of distilling and removing unreacted butyl alcohol and by-products of the reaction such as 2-ethylhexyl alcohol may be further included after conducting the transesterification reaction.

The distillation may be a two-step distillation for separately purifying the butyl alcohol and the by-products of the reaction by using the difference of boiling points.

Alternatively, the distillation may be a mixture distillation. In this case, the ester composition including a desired component ratio may be confirmed relatively stably. The mixture distillation is conducted by distilling the butyl alcohol and the by-products at the same time.

An ester composition prepared by the above-described method is provided in the present invention.

In addition, a resin composition including the ester composition and a resin is provided in the present invention.

In accordance with an example embodiment of the inventive concept, the ester composition is added as a plasticizer.

In accordance with an example embodiment of the inventive concept, the resin may include known resins in the art. For example, at least one selected from the group consisting of ethylene vinyl acetate, polyethylene, polypropylene, polyvinyl chloride, polystyrene, polyurethane, thermoplastic elastomer and polylactic acid may be used, and the resin is not limited thereto.

In accordance with an example embodiment of the inventive concept, 5 to 100 parts by weight of the ester composition may be included based on 100 parts by weight of the resin.

In accordance with an example embodiment of the inventive concept, the resin composition may further include a filler.

The filler may be included by 0 to 300 parts by weight, preferably, 50 to 200 parts by weight, and more preferably, 100 to 200 parts by weight based on 100 parts by weight of the resin.

In accordance with an example embodiment of the inventive concept, the filler may include known fillers in the art, and is not limited thereto. For example, at least one selected from the group consisting of silica, magnesium carbonate, calcium carbonate, calcium carbonate light, talc, magnesium hydroxide, titanium dioxide, magnesium oxide, calcium hydroxide, aluminum hydroxide, aluminum silicate, magnesium silicate and barium sulfate, or a mixture thereof.

In accordance with an example embodiment of the inventive concept, other additive such as a stabilizer may be further included in the resin composition.

The other additive such as the stabilizer may be included by 0 to 20 parts by weight, and preferably 1 to 15 parts by weight based on 100 parts by weight of the resin.

In accordance with an example embodiment of the inventive concept, the stabilizer may include calcium-zinc (Ca—Zn)-based stabilizer such as calcium-zinc complex stearate. However, the stabilizer is not limited thereto.

In accordance with an example embodiment of the inventive concept, the resin composition may further include at least one plasticizer composition selected from the group consisting of dioctyl phthalate (DOP), dibutyl phthalate (DBP), dioctyl terephthalate (DOTP), diisononyl phthalate (DINP), diisodecyl phthalate (DIDP) and di-(2-ethylhexyl) terephthalate (DEHTP). The amount of the plasticizer composition may be 0 to 150 parts by weight, and preferably, 5 to 100 parts by weight based on 100 parts by weight of the resin.

The absorption time of the ester composition in the resin composition is from 3 minutes to 10 minutes, preferably, from 3 minutes to 8 minutes, and more preferably, from 4 minutes to 7 minutes. Within the above-described range, the workability and processability are good.

The absorption time may be evaluated by measuring the time period by using a mixer (Brabender, P600), necessary for mixing the resin and the ester composition and stabilizing the torque of the mixer under the conditions of 77° C. at 60 rpm.

The stabilization of the torque may be obtained as follows. To measure the absorption time, the resin is put into the mixer first and then the ester composition is put. Initially, the peak of the torque is increased and then gradually decreased to maintain almost horizontal state. This state may be confirmed from a graph on a monitor.

The sol viscosity of the resin composition is 4,000 to 15,000 cp, from 5,000 to 11,000 cp, or from 6,000 to 9,000 cp. Within the above-described range, a stable processability may be confirmed.

The sol viscosity of the resin composition base may be measured by using a viscometer of Brookfield (LV type) at 6 rpm and 12 rpm, and the spindle used is #4. A sample may be obtained by mixing, for example, 100 phr of PVC (PB900, LG Chem. Ltd.), 75 phr of an ester composition (plasticizer), 4 phr of a stabilizer (KSZ111XF), 3 phr of a foaming agent (W1039), 13 phr of $TiO_2$ (TMCA100), 130 phr of $CaCO_3$ (OMYA10), 10 phr of a viscosity dropping agent (Exa-sol), and 1 phr of a dispersing agent (BYK3160) to prepare a plastisol. After storing the sample at 25° C. for 1 hour, the viscosity may be measured.

The resin composition may be obtained by decreasing the amount of the viscosity dropping agent when compared to a common composition. Alternatively, the resin composition may exclude the viscosity dropping agent, that is, the resin composition may be the viscosity dropping agent-free resin composition.

The viscosity dropping agent-free resin composition means a composition excluding the viscosity dropping agent for controlling the viscosity of the resin composition.

The ester composition in accordance with an example embodiment of the inventive concept may have a short absorption time with respect to the resin and a short fusion time to improve the processability of the resin, and providing good physical properties when manufacturing a sheet and a compound such as a cable, an interior of a car, a film, a sheet, a tube, a wallpaper, a toy, a flooring material, and the like.

Particularly, when the resin composition including the ester composition is used for manufacturing a wallpaper sheet, good physical properties may be provided.

Hereinafter, reference will be made in detail to embodiments. In this regard, the present embodiments may have different forms and should not be construed as being limited to the descriptions set forth herein. Accordingly, the embodiments are merely described below to explain aspects of the present description. The present embodiments are provided to completely explain the present invention to a person having average knowledge and skilled in the art.

EXAMPLES

Hereinafter, the present invention will be explained further referring to examples and experimental examples, however, the present invention is not limited thereto.

Example 1

Into a reactor equipped with a stirrer, a condenser and a decanter, 1,000 g of di-(2-ethylhexyl)terephthalate (DEHTP) was added, and the temperature was increased to 160° C. Then, 1.6 g of titanium-based catalyst, tetra isopropyl titanate (TIPT) was added as a catalyst, and 40 g of butyl alcohol (4 parts by weight based on 100 parts by weight of DEHTP) was transported by using a pump and added into the reactor. Transesterification reaction was conducted at 160° C. for 3 hours to obtain a reaction product including 0.5 wt % of dibutyl terephthalate (DBTP), 14.5 wt % of 1-butyl 4-(2-ethylhexyl)terephthalate (BEHTP) and 85 wt % of di-(2-ethylhexyl)terephthalate (DEHTP).

A mixture distillation of the reaction product was conducted to remove remaining butyl alcohol and 2-ethylhexyl alcohol and to prepare a final ester composition.

In the transesterification reaction in Example 1, the production amounts (%) of DBTP according to the amounts added of the butyl alcohol are illustrated in the following Table 1.

Example 2

The same procedure explained in Example 1 was conducted except that 5 parts by weight of the butyl alcohol was used based on 100 parts by weight of the DEHTP to prepare an ester composition having a component ratio illustrated in the following Table 1.

Example 3

The same procedure explained in Example 1 was conducted except that 8 parts by weight of the butyl alcohol was used based on 100 parts by weight of the DEHTP to prepare an ester composition having a component ratio illustrated in the following Table 1.

Example 4

The same procedure explained in Example 1 was conducted except that 10 parts by weight of the butyl alcohol was used based on 100 parts by weight of the DEHTP to prepare an ester composition having a component ratio illustrated in the following Table 1.

Example 5

The same procedure explained in Example 1 was conducted except that 15 parts by weight of the butyl alcohol was used based on 100 parts by weight of the DEHTP to prepare an ester composition having a component ratio illustrated in the following Table 1.

Example 6

The same procedure explained in Example 1 was conducted except that 20 parts by weight of the butyl alcohol was used based on 100 parts by weight of the DEHTP to prepare an ester composition having a component ratio illustrated in the following Table 1.

Example 7

The same procedure explained in Example 1 was conducted except that 23 parts by weight of the butyl alcohol was used based on 100 parts by weight of the DEHTP to prepare an ester composition having a component ratio illustrated in the following Table 1.

Comparative Example 1

The same procedure explained in Example 1 was conducted except that 2 parts by weight of the butyl alcohol was used based on 100 parts by weight of the DEHTP to prepare an ester composition having a component ratio illustrated in the following Table 1.

Comparative Example 2

The same procedure explained in Example 1 was conducted except that 28 parts by weight of the butyl alcohol was used based on 100 parts by weight of the DEHTP to prepare an ester composition having a component ratio illustrated in the following Table 1. In this case, a portion of the butyl alcohol was confirmed to be lost during refluxing due to the addition of a large amount of the butyl alcohol.

Comparative Example 3

The same procedure explained in Example 1 was conducted except that 35 parts by weight of the butyl alcohol was used based on 100 parts by weight of the DEHTP to prepare an ester composition having a component ratio illustrated in the following Table 1. In this case, a portion of the butyl alcohol was confirmed to be lost during refluxing due to the addition of a large amount of the butyl alcohol as in Comparative Example 2.

TABLE 1

| | Amount of butyl alcohol (parts per weight) | DBTP (Chemical Formula 1) (wt %) | BEHTP (Chemical Formula 2) (wt %) | DEHTP (Chemical Formula 3) (wt %) |
|---|---|---|---|---|
| Example 1 | 4 | 0.5 | 14.5 | 85.0 |
| Example 2 | 5 | 1.0 | 15.8 | 83.2 |
| Example 3 | 8 | 2.1 | 24.2 | 73.7 |
| Example 4 | 10 | 2.8 | 28.4 | 68.8 |
| Example 5 | 15 | 4.8 | 35.1 | 60.1 |
| Example 6 | 20 | 8.5 | 42 | 49.5 |
| Example 7 | 23 | 9.5 | 43.8 | 46.7 |
| Comparative Example 1 | 2 | 0.1 | 7.9 | 92.0 |
| Comparative Example 2 | 28 | 10.5 | 45.7 | 43.8 |
| Comparative Example 3 | 35 | 15.2 | 47.3 | 37.5 |

Experimental Example 1

Measuring Amount of Ester Composition

In the ester compositions in accordance with Examples 1 to 7 and Comparative Examples 1 to 3, the amounts (wt %) of the DBTP, the BEHTP and the DEHTP were measured by using a gas chromatography (Agilent 7890 GC, column: HP-5, carrier gas; helium).

In the ester compositions of Examples 1 to 7, ether was not detected.

From the result, the component ratios of the reactant, that is, the butyl alcohol and the products, the DBTP, the BEHTP and the DEHTP, and particularly, BEHTP/DBTP may be obtained. In the ester compositions of Examples 1 to 7, BEHTP/DBTP was confirmed to be in the range of 4.6 to 29. In addition, as known from the Table 1, according to the increase of the amount added of the butyl alcohol, the amounts of the DBTP and the BEHTP in the ester composition were gradually increased, and correspondingly, the amount of the DEHTP was decreased.

However, when the amount added of the butyl alcohol exceeds 23 parts per weight based on the DEHTP as in Comparative Example 2, the butyl alcohol was evaporated during conducting the transesterification reaction and the butyl alcohol was lost. Thus, the amount of the DBTP exceeded 9.5, and the production amount of the DBTP was rapidly increased.

Experimental Example 2

Manufacturing Sample (Sheet) and Evaluating Performance

The ester compositions prepared in Examples 1 to 7 and Comparative Examples 1 to 3 were used. 100 pars by weight of polyvinyl chloride resin (PVC (LS 130s)), 55 parts by weight of a plasticizer (the ester composition), 2 parts by weight of a BZ stabilizer (BZ210, Songwon Industrial Co., Ltd.) as an additive and 2 parts by weight of an epoxidized soybean oil (ESO, Songwon Industrial Co., Ltd.) were mixed at 1,300 rpm at 100° C. The process was conducted by using a roll mill at 175° C. for 4 minutes, and by using a press at 185° C. for 3 minutes (under a low pressure) and for 2 minutes and 30 seconds (under a high pressure) to manufacture a sheet having a thickness of 2 mm.

With respect to the sheet, the hardness, the tensile strength, the elongation rate, the migration loss, the sheet weight loss after heating, the heat stability, the accelerated weathering (QUV), and the absorption time were evaluated, and the fusion test was conducted.

The evaluating conditions of each performance are as follows.

Measurement of Hardness

Shore hardness was measured at 25° C. by ASTM D2240.

Measurement of Tensile Strength

The cutting point of the sample was measured after pulling the sample at a cross head speed of 200 mm/min by using a test instrument, U.T.M (Instron, model name: 4466) by the method of ASTM D638. The tensile strength was calculated by the following equation.

Tensile strength(kgf/mm$^2$)=load value(kgf)/(thickness (mm)×width(mm))

Measurement of Elongation Rate

The cutting point of the sample was measured after pulling the sample at a cross head speed of 200 mm/min by using the U.T.M by the method of ASTM D638. The elongation rate was calculated by the following equation.

Elongation rate(%)=length after elongation/initial length×100

Measurement of Migration Loss

A sample having a thickness of 2 mm was obtained by KSM-3156, and ABS (natural color) was attached on both sides of the sample. Then, the weight of 1 kgf/cm$^2$ was applied. The sample was stood in a hot air circulating oven (80° C.) for 72 hours, and cooled at room temperature for 4 hours. Then, the ABS attached on both sides of the sample was removed. The weights of the sample before and after standing in the oven were measured, and the migration loss was calculated by the following equation.

Migration loss(%)={(initial weight of sample at room temperature−weight of sample after standing in oven)/initial weight of sample at room temperature}×100

Measurement of Sheet Weight Loss after Heating

The thus manufactured sample was processed at 70° C. for 72 hours, and the weight of the sample was measured.

Weight loss after heating(wt %)={(initial weight of sample−weight of sample after processing at 70° C. for 72 hours)/initial weight of sample}×100

Measurement of Heat Stability

The heat stability was measured by conducting at 230° C. at 20 mm/30 seconds.

Measurement of QUV

According to NIKE #37 evaluation method, the sheet sample (10*10 cm sample) was stood for 200 hours in a QUV apparatus of Q-panel Company under the following conditions.

QUV conditions: UV lamp: UVA-340/room temperature 22±2° C.

The measurement was conducted using a spectrometer (UV-3600).

Measurement of Absorption Time

PVC (LS 130s) and an ester composition (plasticizer) were mixed by using a mixer (Brabender) under mixing conditions of 77° C. at 60 rpm. The time period from mixing the resin and the ester composition (plasticizer) to obtaining a stabilized state of the torque of the mixer was measured and evaluated.

The stabilization of the torque may be obtained as follows. The resin is put first into the mixer and then the ester composition is put to measure the absorption time. Initially, the peak of the torque is increased and then gradually decreased to maintain an almost horizontal state. This state may be confirmed from a graph on a monitor.

Fusion Test

The fusion test was conducted with the mixed sample after processing under the conditions of 110° C./60 g/70 rpm.

The performance for samples obtained by using the ester compositions according to Examples 1 to 7 and Comparative Examples 1 to 3 and by using dioctyl phthalate (DOP) alone, diisononyl phthalate (DINP) alone, and dibutyl terephthalate (DBTP) alone was obtained and compared.

The performance test results by the above-described methods are illustrated in the following Table 2. In Table 2, C Example denotes Comparative Example, and Ref denotes reference.

TABLE 2

| Performance test | Ex. 1 | Ex. 2 | Ex. 3 | Ex. 4 | Ex. 5 | Ex. 6 | Ex. 7 | C Ex. 1 | C Ex. 2 | C Ex. 3 | DOP | DNP | DBTP |
|---|---|---|---|---|---|---|---|---|---|---|---|---|---|
| Shore hardness (Shore "A") | 76.0 | 75.6 | 75.0 | 74.2 | 73.4 | 73.2 | 73.1 | 78.3 | 72.9 | 71.5 | 72.5 | 76.8 | 69.8 |
| Tensile strength (kg/mm$^2$) | 2.16 | 2.16 | 2.15 | 2.13 | 2.09 | 2.09 | 2.07 | 2.16 | 2.06 | 2.05 | 2.12 | 2.07 | 1.93 |
| Elongation rate (%) | 387 | 395 | 411 | 421 | 425 | 430 | 432 | 371 | 435 | 442 | 454 | 427 | 454 |
| Migration loss (%) | 3.60 | 3.59 | 3.56 | 3.78 | 4.02 | 4.26 | 4.32 | 3.54 | 6.58 | 7.65 | 3.95 | 3.29 | 10.56 |
| Weight loss after heating (%) | 0.21 | 0.22 | 0.25 | 0.32 | 0.75 | 0.95 | 0.99 | 0.22 | 2.30 | 2.62 | 0.33 | 0.24 | 3.17 |
| Heat stability | Good | Good | Good | Good | Good | Good | Good | Good | Good | Same | Ref | Good | Good |
| QUV | Light yellow | Same | Same | Same | Same | Same | Same | Light yellow | Light yellow | Bad | Ref | Same | Bad |
| Absorption time (sec) | 6' 34 | 6' 27 | 6' 15 | 5' 45 | 5' 03 | 4' 32 | 4' 15 | 7' 08 | 3' 44 | 2' 42 | 5' 06 | 6' 20 | 1' 40 |
| Fusion test (sec) | 102 | 75 | 50 | 48 | 42 | 39 | 36 | 138 | 32 | 28 | 32 | 45 | 22 |

As illustrated in Table 2, the sheets obtained by using the ester compositions including 0.5 to 9.5 wt % of the DBTP according to Examples 1 to 7 were confirmed to illustrate preferable results in all physical properties, when compared with the sheets obtained by using the ester compositions according to Comparative Examples 1 to 3, and by using the dioctyl phthalate (DOP) alone, the diisononyl phthalate (DINP) alone, and the dibutyl terephthalate (DBTP) alone.

Particularly, the hardness, the elongation rate, the absorption time and the fusion properties were confirmed good for Examples 1 to 7 of the present invention when compared with Comparative Example 1.

When considering the good properties of the absorption time, the fusion properties and the hardness as illustrated for Examples 1 to 7, finally manufactured products may possibly result a great difference in physical properties. In addition, when the ester compositions of Examples 1 to 7 are practically applied for manufacturing a sheet, the amount of the ester composition may be decreased, and the stability of good process workability for manufacturing a final product may be provided.

When the absorption time or the fusion properties are too low as for Comparative Example 1, the workability may be bad and the productivity may be decreased. On the contrary, when the absorption time and the fusion properties are too high as for Comparative Examples 2 and 3, working time may be decreased due to rapid gelling of the resin in the mixture. In this case, a high mixing frequency may be necessary and the workability may be decreased.

Referring to Comparative Examples 2 and 3, as the amounts of the DBTP and the BEHTP increase, the migration loss and the weight loss after heating are rapidly increased. These properties may become fatal defects in the processability and the long-period stability of a final product.

With respect to the weight loss after heating, several times of the amount was measured for Comparative Examples 2 and 3 when compared with Examples 1 to 7. Particularly, the weight loss after heating for Comparative Examples 2 and 3 was about 10 times or above when compared with Examples 1 to 3.

With respect to the heat stability and the QUV test, the same results were obtained for Examples 2 to 7 as the case using the DOP alone. The heat stability for each of Examples 1 to 7 was good with reference to the case using the DOP alone.

For Comparative Examples 2 and 3 in which the amounts of the DBTP were less than 0.5 wt % or exceeded 9.5 wt %, the QUV results were slightly bad or poor, and the heat stability was slightly good or the same when compared with the case using the DOP alone.

The absorption times with respect to the resin for Examples 1 to 7 were good or at least the same when compared with the case using the DOP, or the DINP. The DBTP has a relatively rapid absorption time and may function to deteriorate the physical properties of a product when applied to a practical product such as a sheet. When the absorption time is too fast, a sufficient time for processing the product may not be confirmed, and undesired product loss may be generated.

Therefore, when the ester compositions including the DBTP by 0.5 to 9.5 wt % according to Examples 1 to 7 are applied for the manufacture of a sheet, physical properties such as the hardness, the tensile strength, the elongation rate, the migration loss, the weight loss after heating, the heat stability, the QUV, the absorption time and the fusion test result, are good when compared with the cases using the DOP alone, the DINP alone, the DBTP alone, and the ester compositions according to Comparative Examples 1 to 3.

Experimental Example 3

Manufacturing Sample (Compound) and Evaluating Performance 50 parts by weight of the ester compositions prepared in Examples 1 to 7 and Comparative Examples 1 to 3 based on 100 parts by weight of polyvinyl chloride resin (PVC (LS100)), 5 parts by weight of RUP144 (Adeka Korea Co.), 40 parts by weight of Omya 1T (Omya), and 0.3 phr of St-A (Isu Chemical Co., Ltd.) were mixed at 100° C. at 1,300 rpm. The process was conducted using a roll mill at 175° C. for 4 minutes and using a press at 185° C. for 3 minutes (under a low pressure) and for 2 minutes and 30 seconds (under a high pressure) to manufacture a sample having a thickness of 2 mm.

With respect to the sample, the hardness, the tensile strength, the elongation rate, the sheet weight loss after heating, and the accelerated weathering (QUV), were evaluated and the stress test and the fusion test were conducted. The performance test results with respect to the samples are illustrated in the following Table 3.

In this case, the stress test was conducted by the following conditions.

Stress test: The sample of bent state was stood for 7 days at room temperature, and migration and deformed degree were observed.

In Table 3, C Example denotes Comparative Example, Ref denotes reference, RT denotes room temperature, and "○" denotes normal.

TABLE 3

| Performance evaluation | | Ex. 1 | Ex. 2 | Ex. 3 | Ex. 4 | Ex. 5 | Ex. 6 | Ex. 7 | C Ex. 1 | C Ex. 2 | C Ex. 3 | DOP | DNP | DBTP | note |
|---|---|---|---|---|---|---|---|---|---|---|---|---|---|---|---|
| Shore hardness (Shore "A") | | 82.7 | 82.4 | 82.3 | 81.2 | 81.0 | 80.6 | 80.2 | 84 | 80.5 | 79.2 | 81.5 | 83.5 | 78 | RT |
| RT | Tensile strength (kg/mm$^2$) | 1.86 | 1.75 | 1.68 | 1.60 | 1.58 | 1.55 | 1.52 | 1.88 | 1.38 | 1.32 | 1.64 | 1.60 | 1.29 | 200 mm/min |
| | Elongation rate (%) | 291 | 290 | 288 | 280 | 275 | 274 | 270 | 302 | 257 | 234 | 286 | 287 | 232 | |
| After heating (100° C. × | Tensile strength (kg/m$^2$) | 1.66 | 1.63 | 1.66 | 1.65 | 1.58 | 1.62 | 1.60 | 1.65 | 1.68 | 1.70 | 1.65 | 1.54 | 1.35 | 100° C. × 16 8 hrs, |

TABLE 3-continued

| Performance evaluation | | Ex. 1 | Ex. 2 | Ex. 3 | Ex. 4 | Ex. 5 | Ex. 6 | Ex. 7 | C Ex. 1 | C Ex. 2 | C Ex. 3 | DOP | DNP | DBTP | note |
|---|---|---|---|---|---|---|---|---|---|---|---|---|---|---|---|
| 168 hrs) | | | | | | | | | | | | | | | 200 mm/min |
| | Elongation rate (%) | 230 | 225 | 209 | 176 | 154 | 148 | 142 | 223 | 62 | 25 | 128 | 200 | 7 | |
| Weight loss after heating (%) | | 0.49 | 0.48 | 0.50 | 0.78 | 1.56 | 1.88 | 1.95 | 0.48 | 7.81 | 8.26 | 3.32 | 0.61 | 18.59 | 100° C. × 16 8 hrs |
| QUV | | Same | Same | Same | Same | Same | Same | Light yellow | Light yellow | Light yellow | Bad | Ref | Same | Light yellow | 200 hrs |
| Stress test | | ○ | ○ | ○ | ○ | ○ | ○ | ○ | Bleeding | ○ | ○ | ○ | ○ | ○ | RT, 7 days |
| Fusion test (sec) | | 110 | 108 | 102 | 95 | 90 | 90 | 88 | 145 | 86 | 82 | 83 | 86 | 80 | 110° C./ 70 rpm |

As confirmed from Table 3, when the ester compositions according to Examples 1 to 7 are applied for the manufacture of compounds, all the physical properties are equally good when compared with the cases using the ester compositions according to Comparative Examples 1 to 3, the dioctyl phthalate (DOP) alone, the diisononyl phthalate (DINP) alone, and the dibutyl terephthalate (DBTP) alone.

Particularly, when the elongation rate was measured at room temperature and after heating with respect to the samples (compounds) obtained by using the ester compositions according to Examples 1 to 7 and Comparative Examples 1 to 3, the elongation rates at room temperature and after heating at 100° C. were good for Examples 1 to 7 when compared with the cases using the DBTP by the amount deviated from the range of 0.5 wt % to 9.5 wt % as in Comparative Examples 2 and 3.

From the result, the elongation rate at room temperature or after heating may be rapidly decreased when the amount of the DBTP exceeds a certain amount, that is, 10 wt % (for example, 10.5 wt %).

In addition, the weight losses after heating for Examples 1 to 7 were in the range of 0.49% to 1.95%, and the weight losses after heating for Comparative Examples 2 and 3 were rapidly increased to the range of 7% to 8.3%. The rapid increase of the weight loss after heating as for Comparative Examples 2 and 3 means the decrease of the ester composition (plasticizer) present in the sample, and results in the deterioration of the elongation rate.

For the samples manufactured by using the ester compositions according to Examples 1 to 7, remarkably excellent or at least the same degrees of the QUV, the stress test and the fusion test were obtained when compared with the cases using the ester compositions according to Comparative Examples 1 to 3 and using the DOP alone, the DINP alone and the DBTP alone, as well as the elongation rate and the weight loss after heating.

Experimental Example 4

Manufacturing Sample (Plastisol) and Evaluating Performance 80 parts by weight of the ester compositions prepared in Examples 1 to 7 and Comparative Examples 1 to 3 based on 100 parts by weight of polyvinyl chloride resin (PVC (PB900, LG Chem. Ltd.)), 90 parts by weight of Omya 10 (Omya) as a filler, 3 parts by weight of K—Zn stabilizer (KKZ 102 PF (Woochang Chemical Co., Ltd.)), 3 parts by weight of DWPX03 (Dongjin Co., Ltd.), 3 parts by weight of BYK4040 (BYK), 10 parts by weight of Dso1240R (Isu Chemical Co., Ltd.) and 12 parts by weight of TiO$_2$ were mixed.

With respect to the plastisol, the heat stability and the fusion test were conducted according to the experimental conditions illustrated in the following Table 4 by similar methods as explained in Experimental Example 1. In this case, the heat stability was evaluated by the following conditions.

Heat stability measurement: 30 mm/20 seconds at 230° C., pregelling at 150° C. for 45 seconds, coating to a thickness of 0.4 mm.

As confirmed in the following Table 4, the results on the heat stability and the fusion test were good for the plastisols obtained by using the ester compositions according to Examples 1 to 7 when compared with the results for the plastisols obtained by using the ester compositions according to Comparative Examples 1 to 3 and by using the dioctyl phthalate (DOP) alone, the diisononyl phthalate (DINP) alone, and the dibutyl terephthalate (DBTP) alone.

Particularly, good properties were confirmed to be obtained with respect to fusion properties for Examples 1 to 7 when compared with the cases using the DOP and the DINP.

The results on the fusion test were designated by the levels of 1 (fast fusion) to 5 (slow fusion). The fusion test levels for Examples 1 to 7 were about 2 and 3 degrees. On the contrary, the fusion test levels for Comparative Examples 2 and 3, and for the DBTP were fast. Due to the fast fusion time, the time necessary for smooth processing a product may be decreased, and a production lost may be generated. In this case, the workability may be rather deteriorated.

On the contrary, too slow fusion time such as for Comparative Example 1 and the DINP, the workability may be deteriorated and productivity may be decreased.

Thus, good physical properties may be obtained and process advantages may be provided when applied in a product for Examples 1 to 7, illustrating appropriate fusion time.

In Table 4, C Example denotes Comparative Example, and Ref denotes reference. The results on the fusion test are expressed by 1 (fast fusion) to 5 (slow fusion).

TABLE 4

| Performance evaluation | Ex. 1 | Ex. 2 | Ex. 3 | Ex. 4 | Ex. 5 | Ex. 6 | Ex. 7 | C Ex. 1 | C Ex. 2 | C Ex. 3 | DOP | DNP | DBTP |
|---|---|---|---|---|---|---|---|---|---|---|---|---|---|
| Heat stability | Good | Good | Good | Good | Good | Good | Good | Good | Good | Good | Ref | Same | Good |
| Fusion test | 3 | 2 | 2 | 2 | 2 | 2 | 2 | 4 | 1 | 1 | 3 | 5 | 1 |

The ester composition of the present invention has a short absorption time with respect to the resin and short fusion time and improves the processability of the resin composition. In addition, good physical properties may be provided when manufacturing a sheet and a compound such as a cable, an interior of a car, a film, a sheet, a tube, a wallpaper, a toy, a flooring material, and the like.

While the present invention has been shown and described in connection with the exemplary embodiments, it will be apparent to those skilled in the art that modifications and variations can be made without departing from the spirit and scope of the invention as defined by the appended claims.

What is claimed is:

1. A resin composition comprising an ester composition and polyvinyl chloride, wherein the ester composition comprises:
   terephthalate compounds substituted with a non-hybrid and non-branched alkyl group, a hybrid and branched alkyl group, and a non-hybrid and branched alkyl group, respectively, by amounts of 0.5 wt % to 9.5 wt %, 14.5 wt % to 43.8 wt %, and 46.7 wt % to 85 wt %, based on a total amount of the ester composition.

2. The resin composition of claim 1, wherein the terephthalate compounds substituted with the non-hybrid and non-branched alkyl group, the hybrid and branched alkyl group, and the non-hybrid and branched alkyl group, respectively by amounts of 1 wt % to 8.5 wt %, 15.8 wt % to 42 wt %, and 49.5 wt % to 83.2 wt %, based on the total amount of the ester composition.

3. The resin composition of claim 1, wherein a weight ratio of the terephthalate compound substituted with the hybrid and branched alkyl group with respect to the terephthalate compound substituted with the non-hybrid and non-branched alkyl group is 4.6 to 29.

4. The resin composition of claim 3, wherein the weight ratio of the terephthalate compound substituted with the hybrid and branched alkyl group with respect to the terephthalate compound substituted with the non-hybrid and non-branched alkyl group is 5 to 17.

5. The resin composition of claim 1, wherein the terephthalate compound substituted with the non-hybrid and non-branched alkyl group is dibutyl terephthalate (DBTP) represented by following Chemical Formula 1:

[Chemical Formula 1]

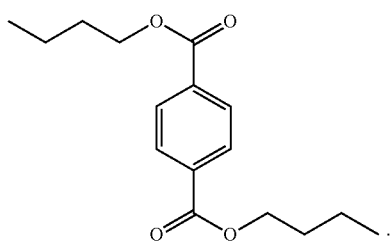

6. The resin composition of claim 1, wherein the terephthalate compound substituted with the hybrid and branched alkyl group is 1-butyl 4-(2-ethylhexyl)terephthalate (BE-HTP) represented by following Chemical Formula 2:

[Chemical Formula 2]

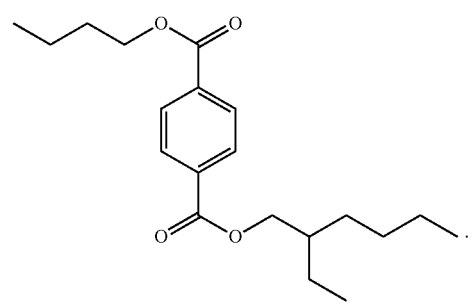

7. The resin composition of claim 1, wherein the terephthalate compound substituted with the non-hybrid and branched alkyl group is di-(2-ethylhexyl)terephthalate (DE-HTP) represented by following Chemical Formula 3:

[Chemical Formula 3]

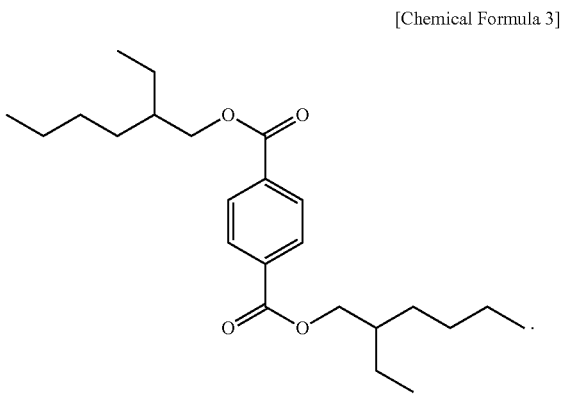 [SMILES: CCCCC(CC)COC(=O)c1ccc(C(=O)OCC(CC)CCCC)cc1 ; "."]

8. The resin composition of claim 1, wherein the ester composition is an ether-free composition.

9. The resin composition of claim 1, wherein an amount of the ester composition is 5 to 100 parts by weight based on 100 parts by weight of the resin.

* * * * *